(12) United States Patent
Hanik

(10) Patent No.: US 12,162,830 B2
(45) Date of Patent: Dec. 10, 2024

(54) ALDEHYDE REMOVAL PROCESS FOR METHANOL CARBONYLATION

(71) Applicant: Celanese International Corporation, Irving, TX (US)

(72) Inventor: Peter Hanik, Houston, TX (US)

(73) Assignee: Celanese International Corporation, Irving, TX (US)

( * ) Notice: Subject to any disclaimer, the term of this patent is extended or adjusted under 35 U.S.C. 154(b) by 573 days.

(21) Appl. No.: 17/598,505

(22) PCT Filed: Apr. 1, 2020

(86) PCT No.: PCT/US2020/026214
§ 371 (c)(1),
(2) Date: Sep. 27, 2021

(87) PCT Pub. No.: WO2020/205997
PCT Pub. Date: Oct. 8, 2020

(65) Prior Publication Data
US 2022/0185760 A1 Jun. 16, 2022

Related U.S. Application Data

(60) Provisional application No. 62/827,290, filed on Apr. 1, 2019.

(51) Int. Cl.
*C07C 51/46* (2006.01)
*B01D 3/14* (2006.01)
*B01D 3/36* (2006.01)

(52) U.S. Cl.
CPC .............. *C07C 51/46* (2013.01); *B01D 3/143* (2013.01); *B01D 3/36* (2013.01)

(58) Field of Classification Search
CPC ........... C07C 51/46; C07C 53/08; B01D 3/36; B01D 3/143; B01D 5/009; B01D 5/0036; B01D 5/0057
See application file for complete search history.

(56) References Cited

U.S. PATENT DOCUMENTS 2,667,450 A 1/1954 Cines
4,383,894 A * 5/1983 Hartmann ............... C07C 45/84
203/70

(Continued)

FOREIGN PATENT DOCUMENTS

WO 2014/070739 A1 5/2014
WO WO 2014/070739 * 5/2014 ............. C07C 51/42

OTHER PUBLICATIONS

International Search Report and Written Opinion for PCT/US20/26214 mailed Jun. 30, 2020, 16 pages.

(Continued)

*Primary Examiner* — Yate' K Cutliff
(74) *Attorney, Agent, or Firm* — Kilpatrick Townsend & Stockton LLP

(57) ABSTRACT

Disclosed is a method for removing acetaldehyde and other permanganate reducing compounds (PRCs) from a process stream in the methanol carbonylation process for making acetic acid. The method includes the steps of forming an azeotrope to reduce the boiling point of the acetaldehyde and other PRCs to facilitate separation of the acetaldehyde and other PRCs from the process. In one embodiment the azeotrope comprises butane and acetaldehyde.

19 Claims, 3 Drawing Sheets

(56) References Cited

U.S. PATENT DOCUMENTS

| | | | |
|---|---|---|---|
| 5,625,095 A | 4/1997 | Miura et al. | |
| 8,969,613 B2 * | 3/2015 | Hallinan | C07C 51/44 |
| | | | 560/231 |
| 2018/0009732 A1 | 1/2018 | Shimizu et al. | |

OTHER PUBLICATIONS

International Preliminary Report on Patentability for PCT/US2020/026214 issued Sep. 28, 2021, all pages.

* cited by examiner

ALDEHYDE REMOVAL PROCESS FOR METHANOL CARBONYLATION

PRIORITY CLAIM

This application is a U.S. National Phase of PCT/US2020/026214, filed Apr. 1, 2020, entitled "Aldehyde Removal Process for Methanol Carbonylation," which claims priority to U.S. Provisional Application No. 62/827,290, filed on Apr. 1, 2019, entitled "Improved Aldehyde Removal Process for Methanol Carbonylation," the entire contents and disclosures of which are hereby incorporated by reference.

FIELD OF THE INVENTION

This invention relates generally to a process for continuous acetic acid production, in particular, to improved processes for removing aldehydes.

BACKGROUND

One of the most common processes used to synthesize acetic acid is the carbonylation of methanol. Preferred methods utilize a catalyst typically a rhodium or iridium salt.

Over the years efforts have been made to lower the amount of water required to stabilize the catalysts. Methods that employ water levels below about 5% or so are referred to as "low water processes." Some of the "low water processes" are described in U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; European Patent No. EP 0 161 874 B2, published Jul. 1, 1992. "Low water processes" require maintaining reactor contents including catalyst and a sufficient amount plus an excess amount of inorganic iodide anion over and above the iodide ion that is present due to hydrogen iodide in the system. It is known in conventional carbonylation processes to use an excess of iodide anion provided through addition of lithium iodide.

Low water processes are desired because they reduce production of undesired products: carbon dioxide and hydrogen. However, other impurities, such as acetaldehyde and its derivatives, are increased in the "low water process". Acetaldehyde and similar carbonyl compounds affect the quality of the acetic acid and because they are recycled through the process, the concentration of acetaldehyde and similar carbonyl compounds (i.e. compounds, with or without saturation, that contain aldehyde or ketone functional groups) can build up over time. Carbonyl impurities decrease the permanganate time of the acetic acid, a quality test commonly used in the industry as described in Haynes A. "Acetic Acid Synthesis by Catalytic Carbonylation of Methanol," *Top Organomet Chem* (2006) 18: 179-205, the entire contents and disclosure of which are incorporated by reference.

There remains a need to improve the carbonylation process to remove acetaldehyde and other light contaminants that build up and end up as contaminants in the finished acetic acid product.

SUMMARY

The embodiments described herein are directed to reducing acetaldehyde and similar compounds such as, acetone, methyl ethyl ketone, butyraldehyde, crotonaldehyde, 2-ethyl crotonaldehyde, and 2-ethyl butyraldehyde and similar compounds. The embodiments of the present invention may also lead to reduction of propionic acid formation in some cases because acetaldehyde formation appears to cause increases in propionic acid levels, perhaps because of the availability of hydrogen in the reactor. It is also possible that impurities are derived from acetaldehyde and these impurities may form more readily in the presence of iodide salts such as lithium iodide. Acetaldehyde also condenses to form unsaturated aldehydes, such as crotonaldehyde, and possibly generating higher alkyl iodides in the system and these are particularly difficult to remove. Furthermore, the largest use of acetic acid is in production of vinyl acetate and higher alkyl iodides are poisonous to the catalysts used in vinyl acetate production.

In one embodiment there is provided a method for removing aldehydes formed in the production of acetic acid, comprising reacting methanol and carbon monoxide in a suitable liquid phase reaction medium comprising a Group VIII metal catalyst, an organic iodide, and water; separating said liquid phase reaction medium, with or without heat, into a volatile phase comprising acetic acid and aldehyde, and a less volatile phase comprising the Group VIII metal catalyst; distilling said volatile phase in a first distillation tower to yield a side draw stream comprising acetic acid and an overhead comprising organic iodide, water, and aldehyde; contacting a portion of said overhead with an azeotropic agent to form one or more azeotropes with at least one of said aldehydes; removing said one or more azeotropes to obtain a return stream containing said organic iodide; and combining said return stream with said less volatile phase, wherein said return stream is deficient in the one or more azeotropes with aldehyde.

In one embodiment there is provided a method for removing aldehydes formed in the production of acetic acid, comprising reacting methanol and carbon monoxide in a suitable liquid phase reaction medium comprising a Group VIII metal catalyst, an organic iodide, and water; separating said liquid phase reaction medium, with or without heat, into a volatile phase comprising acetic acid and aldehyde, and a less volatile phase comprising the Group VIII metal catalyst; distilling said volatile phase in a first distillation tower to yield a side draw stream comprising acetic acid and an overhead comprising organic iodide, water, and aldehyde; collecting a condensed portion of the overhead in an overhead decanter receiver to yield an aqueous phase and an organic phase; contacting at least a portion of said organic phase with an azeotropic agent to form a stream containing one or more azeotropes with at least one of said aldehydes; and fractionating said stream in a second distillation tower to remove aldehydes.

In one embodiment there is provided a method for removing aldehydes formed in the production of acetic acid, comprising reacting methanol and carbon monoxide in a suitable liquid phase reaction medium comprising a Group VIII metal catalyst, an organic iodide, and water; separating said liquid phase reaction medium, with or without heat, into a volatile phase comprising acetic acid and aldehyde, and a less volatile phase comprising the Group VIII metal catalyst; distilling said volatile phase in a first distillation tower to yield a side draw stream comprising acetic acid and an overhead comprising organic iodide, water, and aldehyde; collecting a condensed portion of the overhead in an overhead decanter receiver to yield an aqueous phase and an organic phase; contacting at least a portion of said aqueous phase with an azeotropic agent to form a stream containing one or more azeotropes with at least one of said aldehydes;

and fractionating at least a portion said stream in a second distillation tower to remove aldehydes.

DETAILED DESCRIPTION

Figure 1:
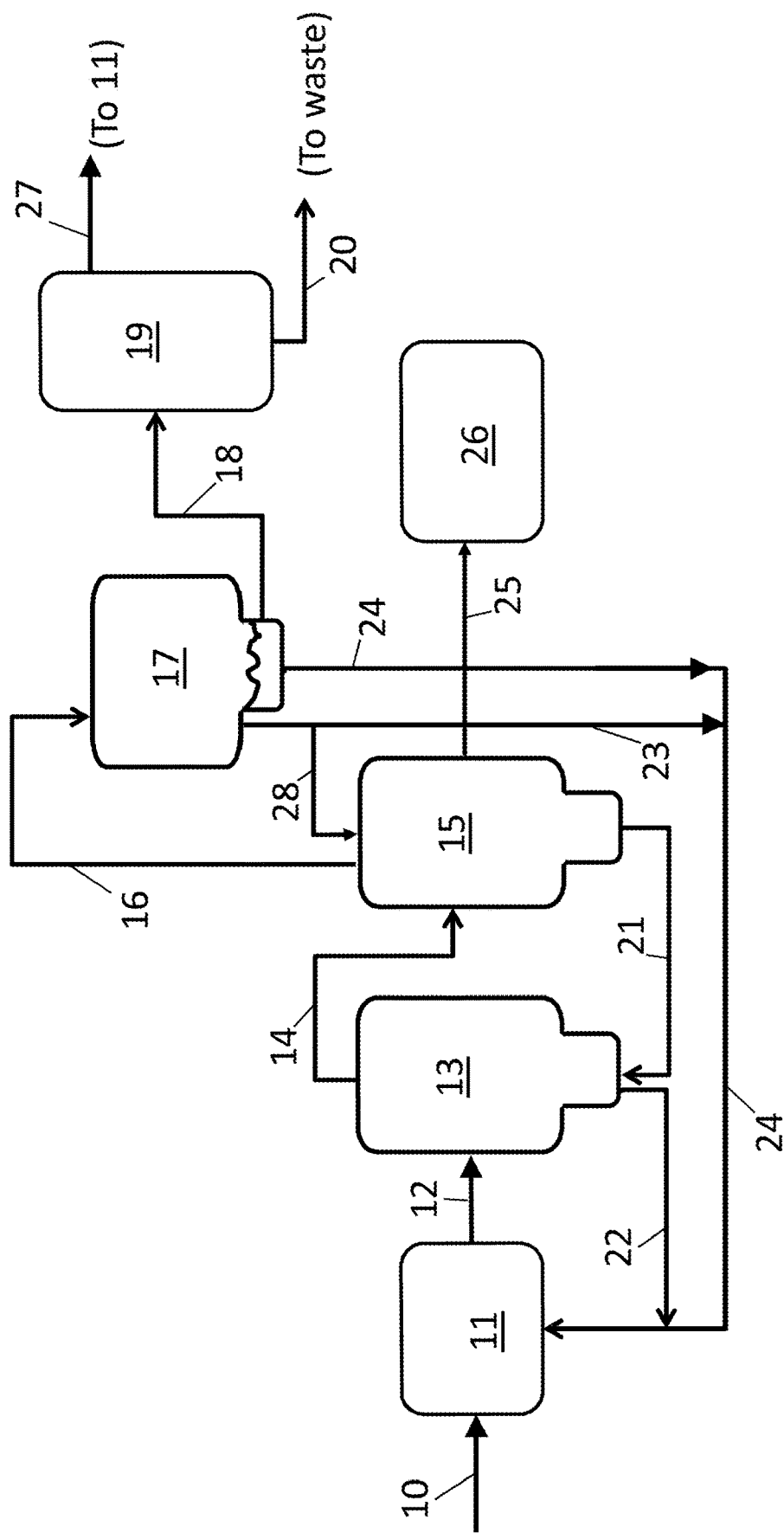
FIG. 1 is a schematic process of a carbonylation process according to various embodiments of the present invention.

At the outset, it should be noted that in the development of any such actual embodiment, numerous implementation—specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. % or % by mass), based on the total weight of the particular stream or composition present, unless otherwise noted. Room temperature is 25° C. and atmospheric pressure is 101.325 kPa unless otherwise noted.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minim is stream as would be readily understood by one of reasonable skill in the art.

It is to be understood that the term "streams" "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

This invention relates to a process for the production of acetic acid and, in particular, an improved process for the reduction and/or removal of acetaldehyde and similar compounds such as, acetone, methyl ethyl ketone, butyraldehyde, crotonaldehyde, 2-ethyl crotonaldehyde, and 2-ethyl butyraldehyde and similar compounds formed by the carbonylation of methanol in the presence of a Group VIII metal carbonylation catalyst to produce acetic acid. More specifically, this invention relates to an improved process for reducing and/or removing acetaldehyde and similar compounds from streams during the formation of acetic acid by said carbonylation processes using an azeotropic agent, such as an alkane azeotropic agent.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The processes described herein relate in general to processes used to carbonylate methanol (or another carbonylatable reactant, including, but not limited to, methyl acetate, methyl formate or dimethyl ether, or mixtures thereof) to acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259, the entire contents and disclosure of which is incorporated by reference.

Generally, the rhodium component of the catalyst system is understood to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide (e.g., organic iodide), and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at "low water" concentrations well below that previously taught by, e.g., U.S. Pat. No. 3,769,329. Accordingly, for a low water process the reaction rates are maintained and/or improved, while operating at water concentrations below 14 wt. % and as low as about 0.1 wt. %. In one embodiment, the water concentration is from 0.1 to less than 14 wt. %, e.g., from 1 to 10 wt. % or from 2 to 8 wt. %.

In accordance with the carbonylation process most useful to manufacture acetic acid according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide being preferred. It has been found, e.g., U.S. Pat. No. 5,001,259, that under low water concentrations, methyl acetate and lithium iodide act as rate promoters only when relatively high concentrations of each of these components are present and that the promotion is higher when both of these components are present simultaneously. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through a liquid phase reaction medium reaction medium containing the Group VIII metal catalyst (e.g., rhodium catalyst), an organic iodide (e.g., methyl iodide), water, and optionally an iodide salt, at conditions of temperature and pressure suitable to form the acetic acid.

In one embodiment, the liquid phase reaction medium may comprise an iodide salt and it will be generally recognized that it is the concentration of iodide ion that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, lithium iodides are useful. In the low water carbonylation process most useful in this invention, the additional iodide ion over and above the iodide ion present as hydrogen iodide is generally present in the catalyst solution in amounts such that the total iodide ion concentration is from about 2 to about 20 wt. % and the methyl acetate is generally present in amounts of from about 0.5 to about 30 wt. %, and the methyl iodide is generally present in amounts of from about 5 to about 20 wt. %. The rhodium catalyst is generally present in amounts of from about 200 to about 2000 parts per million (ppm).

Typical reaction temperatures for carbonylation will be from about 150° C. to about 250° C., with the temperature range of about 180° C. to about 220° C. being a preferred range. The carbon monoxide partial pressure in the reactor can vary widely but is typically about 2 to about 30 atmospheres, and preferably, about 3 to about 10 atm. The hydrogen partial pressure, at an absolute pressure, in the reactor is typically from 0.05 to 5 atm, e.g., from 0.25 to 2 atm or from 0.3 to 1.8 atm. Because of the partial pressure of by-products and the vapor pressure of the contained liquids, the total reactor pressure will range from about 15 to about 40 atmospheres.

The production rate of acetic acid may be from 5 to 50 mol/L·h, e.g., from 10 to 40 mol/L·h, or from 15 to 35 mol/L·h.

A typical process for methanol carbonylation is shown in FIG. 1. Major equipment includes a reactor 11, a flash tank 13, a light ends column (first distillation tower) 15, an overhead decanter receiver 17, a hydrocarbons removal column 19, as well as additional purification equipment 26. Additional equipment, including absorbers, ion resins, extractors, and distillation column may also be used in typical processes. Each piece of equipment may be connected by transfer lines such as pipes and may be aided by pumps. The materials flowing in the transfer lines are referred to as streams. The vessels, pipes, flow conduits, and associated equipment themselves may be made of a zirconium-based materials and alloys that tend to have high corrosion resistance, but may be made of iron-based alloys (stainless steel), nickel-based alloys (HASTELLOY™ or INCONEL™), titanium-based materials and alloys, or aluminum-based materials or alloys.

Raw materials, catalysts and other materials are fed to the reactor 11 in stream 10. Although stream 10 is represented by one line in FIG. 1, it should be understood to those skilled in the art that stream 10 may have several physical transfer lines for each different raw material or catalyst material. In particular, stream 10 comprises methanol and carbon monoxide. Stream 10 may also contain water, a Group VIII metal catalyst (e.g., rhodium or iridium catalyst) and/or an organic iodide (e.g., methyl iodide).

The reactor 11 for carbonylation is typically either a stirred vessel or bubble-column type within which the reacting liquid or slurry contents are maintained automatically at a constant level.

The products of reaction are transferred to the flash tank 13 via stream 12. Stream 12 primarily contains acetic acid, methyl acetate, methanol, carbon monoxide, methyl iodide, hydrogen iodide, acetaldehyde, and other hydrocarbon materials. The flash tank 13 separates a volatile (vapor) phase and a less volatile (liquid) phase, with or without heat. In some embodiments, the flashing may be carried out, either adiabatically or thermostatically, to produce a vapor temperature from 100° C. to 260° C., and a liquid temperature from 80° C. to 200° C. The internal pressure (gauge) of the flash tank 13 may be from 0.5 atm to 5 atm, e.g., from 0.5 atm to 3.5 atm, 0.5 to 2.5 atm, or from 0.5 to 1.5 atm. The volatile (vapor) phase exits from the top of the flash tank 13 via stream 14 which comprises primarily of acetic acid and aldehyde. In one embodiment, volatile (vapor) phase comprises acetic acid, water, methyl iodide, hydrogen iodide, acetaldehyde and lighter components. The less volatile (liquid) phase accumulates in the bottom of the flash tank 13 and comprises the Group VIII metal catalyst. In addition, less volatile (liquid) phase further comprises water, acetic acid, methyl acetate, and heavier components. The Group VIII metal catalyst is preferably removed in the less volatile (liquid) phase by preventing entrainment into the volatile (vapor) phase. The less volatile (liquid) phase is pumped, along with one or more recycle stream from throughout the process, to the reactor 11 via stream 22. Due to the carbon monoxide deficient environment in the flash tank 13, a carbon monoxide containing stream may be introduced into the liquid in the lower portion of the flash tank 13 to maintain catalyst stability.

Stream 14 being the volatile phase containing acetic acid and aldehyde flows to the light ends column 15, which is also referred to as the first distillation tower. To allow for separation, the light ends column 15 may comprise a plate column, a packed column or combination thereof. In the embodiments that use a plate column, the theoretical number of plates may range from 5 to 80 plates, e.g., from 10 to 60 plates or from 15 to 50 plates. The light ends column 15 serves several purposes, including crude acetic acid purification and iodide recycle to the reactor 11. The light ends column separates lighter boiling components such as hydrogen iodide, methyl iodide, methyl acetate from higher boiling components such as acetic acid. Stream 21 is the bottoms stream withdrawn from the light ends column 15 and is returned to the flash tank 13, and is eventually returned to the reactor 11. A side draw stream 25 contains wet acetic acid and is sent to downstream purification 26 which includes a drying column, heavy ends column, guard beds, and other processing equipment to obtain the finish acetic acid product. To maintain the quality of the finish acetic acid product there is a need to remove and/or reduce aldehydes from the process.

Stream 16 is the overhead stream from the light ends column, which primarily contains organic iodide (including methyl iodide) but also contains acetaldehyde, some water, methyl acetate and acetic acid and is sent to a phase separator or overhead decanter receiver 17. Stream 16 may be condensed by one or more condensers (not shown) and the condensed portion of stream 16 is collected in the overhead decanter receiver 17 for separation. Overhead decanter receiver 17 is operated under conditions sufficient to cause phase separation, including operating at a temperature from 0° C. to 40° C. A vent gas (not shown) may be withdrawn from overhead decanter receiver 17 to remove vapors, including non-condensable gases.

Overhead decanter receiver 17 yields an aqueous phase in stream 23 and an organic phase in stream 24, which both contain aldehyde which creates product quality issues unless removed and/or reduced. The aqueous phase may comprise water, methyl acetate, aldehydes, and acetic acid, with minor amounts of methyl iodide. In one embodiment, the aqueous phase may have a water concentration from 50 to 90 wt. %, e.g., from 50 to 80 wt. %, a methyl acetate concentration from 1 to 50 wt. %, e.g., from 1 to 25 wt. %, an acetic acid concentration from 1 to 40 wt. %, e.g., from 1 to 25 wt. %, and a methyl iodide concentration of less than or equal to 10 wt. %, e.g., less than or equal to 5 wt %. The acetaldehyde concentration of the aqueous phase may be from 800 to 6000 ppm, e.g., from 1000 to 4500 ppm. In contrast, the organic phase may comprise methyl iodide, methyl acetate, aldehydes, and acetic acid, with minor amounts of water. In one embodiment, the aqueous phase may have a methyl iodide concentration from 40 to 98 wt. %, e.g., from 50 to 95 wt. %, a methyl acetate concentration from 0.1 to 25 wt. %, e.g., from 0.5 to 20 wt. %, an acetic acid concentration from 0.1 to 10 wt. %, e.g., from 0.2 to 8 wt. %, and a water concentration from 0.01 to 2 wt. %, e.g., from 0.05 to 1.5 wt %. The acetaldehyde concentration of the aqueous phase may be from 400 to 3500 ppm, e.g., from 750 to 3000 ppm. In one embodiment, from 25 to 70% of the overhead stream is removed as the aqueous stream, while 30 to 75% of the overhead stream is removed as the organic stream.

The aqueous phase may be withdrawn from the overhead decanter receiver 17 and is suitable for use as a reflux via stream 28 for the light ends column 15. The reflux ratio may be from 0.5 to 20, e.g., from 1 to 15, or from 1.5 to 12. In some embodiments, a portion of the aqueous phase may be combined with the less volatile phase in stream 22 prior to being recycled to the reactor 11.

As shown in FIG. 1, the heavy phase in the overhead decanter receiver 17, which contains primarily methyl iodide, may be recycled to the reactor 11 via stream 24. In some embodiments, a portion of the heavy phase may be refluxed (not shown) to the light ends column 15. In one embodiment, a portion of the heavy phase in stream 18 is transferred to a hydrocarbons removal column 19 where lighter components are recycled to the reactor 11 via stream 27. The heavier components in stream 20 are typically sent to waste. However, such hydrocarbons removal columns are inefficient in removing and/or reducing aldehyde.

Although effective for producing acetic acid in an efficient the process depicted in FIG. 1 does not have a step for removing aldehydes and without such a process the aldehyde would build up in undesirable amounts. Even at relatively low amounts, aldehyde accumulates as an contaminant in the finished acetic acid product leading to quality issues.

Others have proposed many techniques to remove acetaldehyde impurities. These include treating the acetic acid product streams with oxidizers, water, methanol, ozone, activated-carbon, amines, and the like. For example, amine compounds such as hydroxylamine, react with the carbonyl compounds to form oximes that are then separated from the process. However, amine compounds produce additional unwanted impurities which may increase costs and separation processing. Such treatments may or may not be combined with distillation of the acetic acid.

Other processes to reduce acetaldehyde include distillation of light ends condensed from the light ends stripper column. Such processes typically include a light phase containing primarily water, acetic acid and methyl acetate; or a heavy phase containing primarily methyl iodide, methyl acetate and acetic acid; or a stream formed by combining the light and heavy phase. U.S. Pat. Nos. 6,143,930 and 6,339,171, which are incorporated herein by reference in their entirety, teach that it is possible to significantly reduce the undesirable impurities in the acetic acid product by performing a multi-stage purification on the condensed light ends column overhead. In these patents the light ends overhead is distilled twice, and the acetaldehyde is removed in the overhead of each distillation column and a methyl iodide rich stream is recycled to the reactor. The acetaldehyde-rich distillate obtained after the two distillation steps can be optionally extracted with water to remove the majority of the acetaldehyde for disposal, leaving a significantly lower acetaldehyde concentration in the raffinate that is recycled to the reactor. Additional processes and systems for removing aldehydes and other permanganate reducing compounds are described in U.S. Pat. No. 7,223,886 7,855,306; and 8,076,507, all of which are hereby incorporated by reference. In general, the condensed light ends contain less than 1 weight percent acetaldehyde.

The above-described processes have been used to remove carbonyl impurities from the carbonylation system in order to control acetaldehyde levels and permanganate time. To achieve very low levels of aldehyde impurities the capital and operating costs of these processes tends to be high. At least in part, this is due to the small difference in boiling points between acetaldehyde and methyl iodide and the desire to minimize methyl iodide loss in removal of acetaldehyde from the process. There remains an ongoing need to improve the efficiency of acetaldehyde removal and to reduce the capital and operating cost of acetaldehyde removal in methanol carbonylation processes.

In one embodiment of the present invention there is a provided a process to remove and/or reduce the levels of acetaldehyde and similar compounds such as, acetone, methyl ethyl ketone, butyraldehyde, crotonaldehyde, 2-ethyl crotonaldehyde, and 2-ethyl butyraldehyde and similar compounds that are present in the production of acetic acid by methanol carbonylation compared to using currently available technology. Collectively these compounds are referred to as permanganate reducing compounds (PRCs). By reducing the PRCs, and in particular acetaldehyde, the quality of the acetic acid product may be improved.

Advantageously the embodiments disclosed herein reduce the cost, both operating and capital cost, for removing and/or reducing PRCs, in particular acetaldehyde, that are present in the production of acetic acid by methanol carbonylation compared to using currently available technology.

In one embodiment, the present invention uses an azeotrope to lower the apparent boiling point of acetaldehyde. The apparent boiling point of other PRCs such as, acetone, methyl ethyl ketone, butyraldehyde, crotonaldehyde, 2-ethyl crotonaldehyde, and 2-ethyl butyraldehyde and similar compounds may also be lowered through formation of azeotropes. In some embodiments, the azeotrope comprises an azeotropic agent. In some embodiments, the azeotropic agent comprises from 60 to 100%, preferably from 75 to 100%, of a $C_4$ to $C_{20}$ alkane. Preferably the alkane that is selected is an alkane that forms a low boiling point azeotrope with aldehydes, and in one embodiment butane is a suitable alkane. In some embodiments, the alkane may form heterogeneous azeotropes with water to form two liquid phases. The azeotropic agent may also comprise organic compounds and/or water that are accumulating when reusing the azeotropic agent. In some embodiments the azeotropic agent is butane and the azeotrope comprises a butane-acetaldehyde azeotrope. Butane and acetaldehyde form an azeotrope which comprises about 16% acetaldehyde and about 84% butane. The butane acetaldehyde azeotrope also is immiscible in water further facilitating its separation for selected streams in the process.

The boiling points of selected components in the light ends column overhead are shown in Table 1.

TABLE 1

| Boiling points of major components | |
|---|---|
| Compound | Boiling Point, ° C. |
| Acetic Acid | 118 |
| Water | 100 |
| Methyl Iodide | 42 |
| Acetaldehyde | 21 |
| Butane | 0 |
| Butane/Acetaldehyde Azeotrope | −7 |

As shown in Table 1 azeotrope of butane/acetaldehyde have a boiling point lower than the organic iodide (including methyl iodide). Thus, it is preferred to form azeotropes with aldehyde that have a lower boiling point to further remove and/or reduce aldehyde concentrations.

Figure 2:
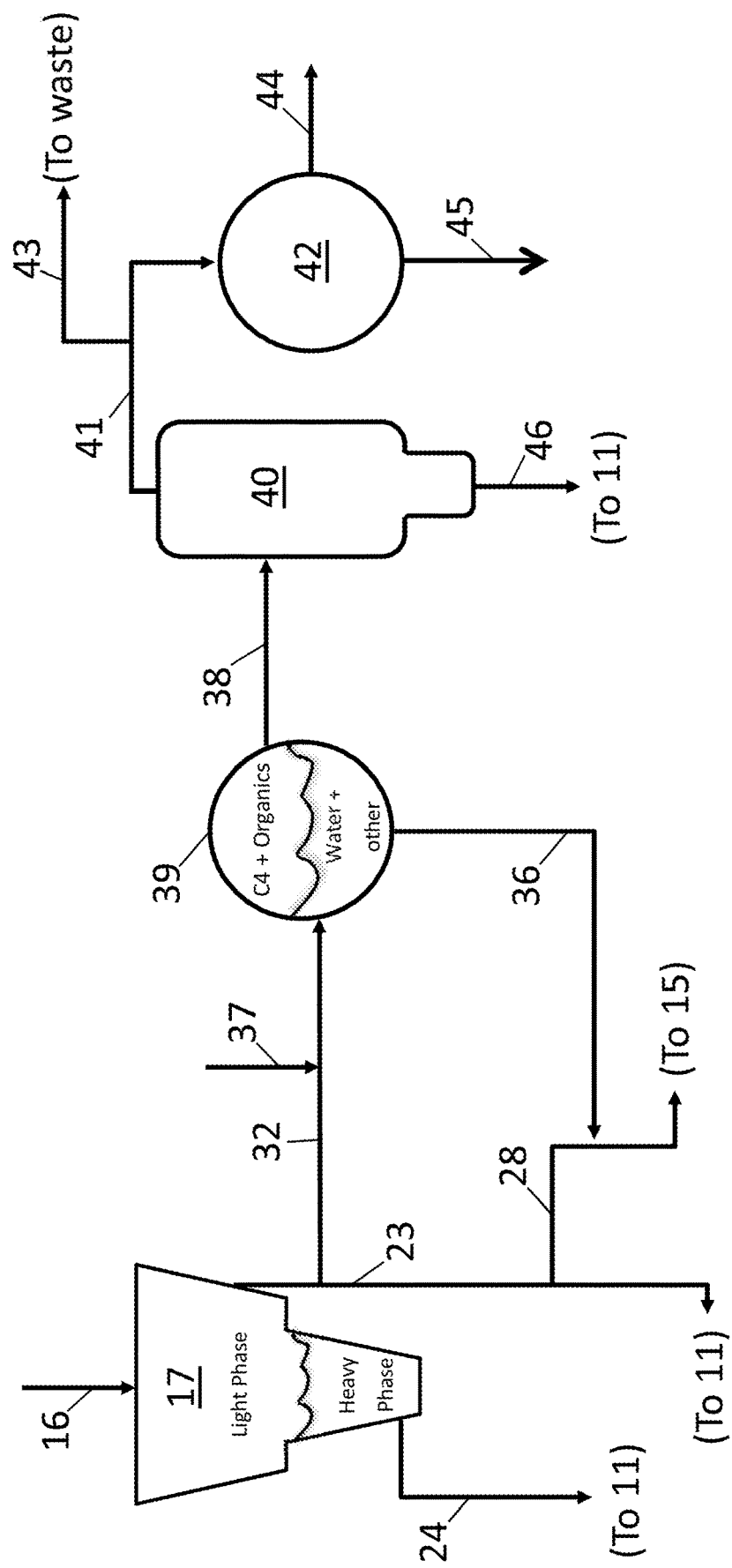
FIG. 2 is a schematic process for removing acetaldehyde by contacting an aqueous stream with an azeotropic agent according to various embodiments of the present invention.
Figure 3:
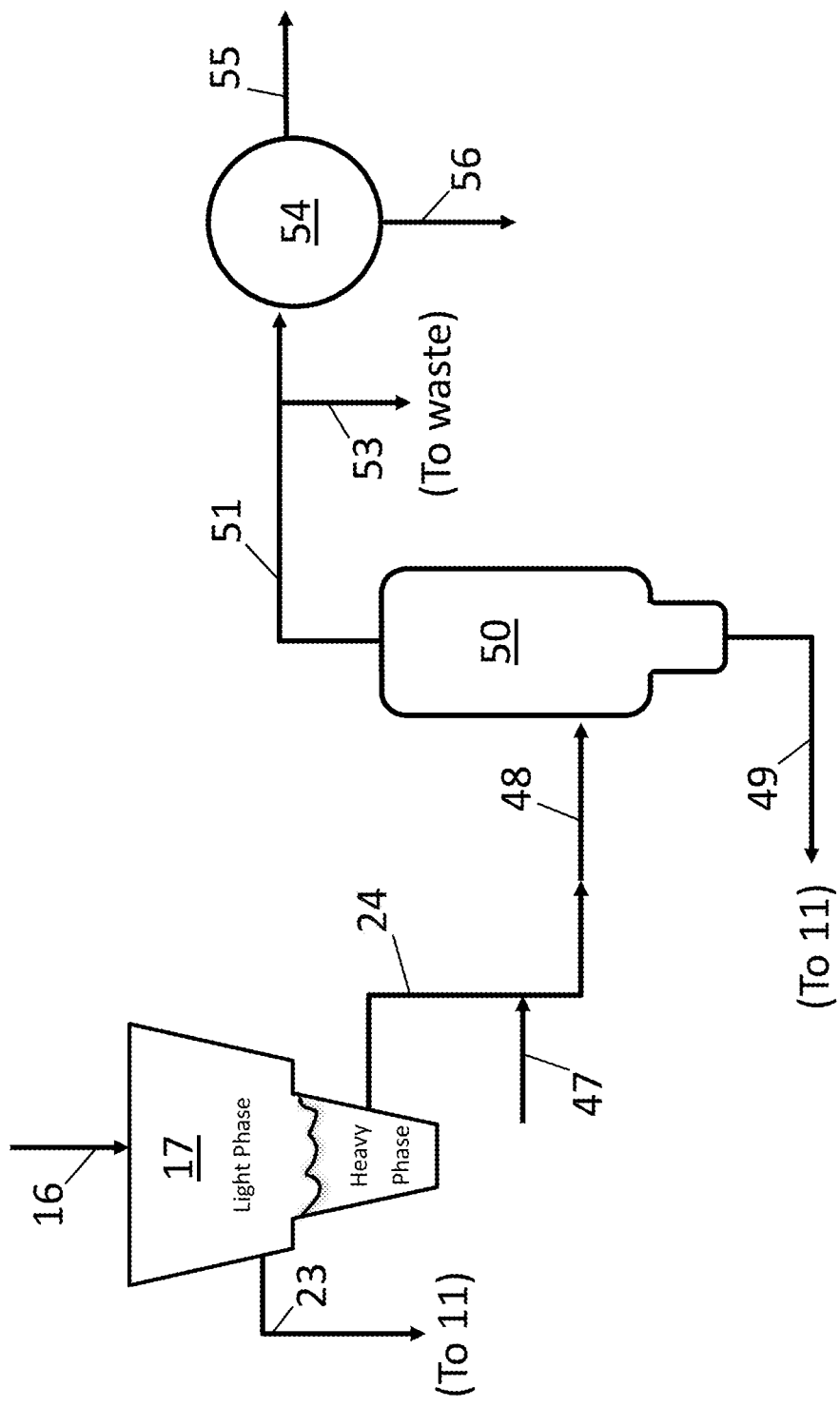
FIG. 3 is a schematic process for removing acetaldehyde by contacting an organic stream with an azeotropic agent according to various embodiments of the present invention.

The embodiments for contacting a stream containing acetaldehyde with an azeotropic agent is shown in FIGS. 2 and 3. In one embodiment, the azeotropic agent is added after, e.g., downstream from, the overhead decanter receiver 17 to the aqueous and/or organic phase being treated for aldehyde removal. Both phases may be treated independently, or the phases may be treated together. Any stream in the process having a suitably high concentration of acetaldehyde and/or similar compounds such as, acetone, methyl ethyl ketone, butyraldehyde, crotonaldehyde, 2-ethyl crotonaldehyde, and 2-ethyl butyraldehyde and similar may be selected for the process. For purposes of the present disclosure a high concentration is greater than or equal to 500 ppm, e.g., greater than or equal to 1000 ppm or greater than or equal to 1500 ppm. Generally, the overhead stream 16 from the light ends column 15 contains a suitably high aldehyde concentration. Even after phase separation, both of the aqueous and organic phases may be further enriched and contain suitably high acetaldehyde concentration.

In FIG. 2 stream 16 is the overhead from the light ends column (first distillation tower). Stream 16 typically contains in the range of 500 to 5000 ppm of acetaldehyde, e.g., from 100 to 4500 ppm of aldehyde, and is a good candidate for removal of acetaldehyde and similar compounds. An overhead decanter receiver 17 is typically used to collect the condensed overhead in stream 16. Two variations in process design for the aldehyde removal process 30 are described herein.

In one embodiment, there is provided a method for removing aldehydes formed in the production of acetic acid, comprising reacting methanol and carbon monoxide in a suitable liquid phase reaction medium comprising a Group VIII metal catalyst (rhodium), an organic iodide (methyl iodide), and water; separating said liquid phase reaction medium, with or without heat, into a volatile phase comprising acetic acid and aldehyde, and a less volatile phase comprising the Group VIII metal catalyst; distilling said volatile phase in a first distillation tower to yield a side draw stream comprising acetic acid and an overhead comprising organic iodide, water, and aldehyde; collecting a condensed portion of the overhead in an overhead decanter receiver to yield an aqueous phase and an organic phase; contacting at least a portion of said aqueous phase with an azeotropic agent to form a stream containing one or more azeotropes with said aldehyde; and fractionating said stream in a second distillation tower to remove aldehydes.

As shown in FIG. 2, the aqueous phase of the overhead decanter receiver 17 for aldehyde reduction flows out as stream 23 and a portion thereof is taken as stream 32 to remove aldehydes. In some embodiments, stream 32 may also comprise a portion of the heavy phase in stream 24, e.g., from 5 to 40% of the heavy phase. In one embodiment, the aqueous phase may comprise aldehyde (acetaldehyde) in the range from 800 to 6000 ppm, e.g., from 1000 to 4500 ppm. As discussed above, a portion of the aqueous phase may be used for reflux in stream 28 on the light ends column (first distillation tower) or recycled to the reactor in stream 23. An azeotropic agent comprising butane from stream 37 is combined and/or mixed with the remainder of stream 32 and fed into a separator 39. The separator 39 may be a simple vessel or a decanter or it may consist of several separation stages. In one embodiment, the amount of azeotropic agent combined with stream 32 is sufficient to form azeotropes with more than 60% of the aldehydes, e.g., more than 80% of the aldehydes. The amount of free aldehyde, i.e., aldehyde not present in an azeotrope, is reduced in stream 32. A suitable mixer or agitator may be used to intimately contact the azeotropic agent to ensure formation of the azeotropes. In one embodiment, the separator 39 is maintained at a temperature from 25° C. to 120° C., e.g., from 30° C. to 100° C.

Two streams are obtained from out of the separator 39. Butane and most of the organic compounds, including the azeotropes with aldehyde, exit via stream 38. Water and traces of other compounds exit via stream 36. Stream 36 can be combined with reflux stream 28. Stream 38 is fed to a fractionator 40, also referred to as a second distillation tower, which may consist of one or more stages or it may be a packed column. The bottom stream from the fractionator 40 contains methyl iodide and is returned to the reactor via stream 46 (return stream). In one embodiment, return stream 46 may be combined with the less volatile phase in FIG. 1, which are together returned to the reactor 11. Stream 46 is deficient in the azeotropes formed with acetaldehyde. Thus, by recycling stream 46 with a deficient amount of acetaldehyde the aldehyde concentration in the reactor 11 may be reduce leading to improve quality acetic acid. For purposes of the present disclosure a deficient or a deficient amount is an unenriched portion or a portion containing less azeotropes formed with acetaldehyde after being contacted with the azeotropic agent (butane).

The overhead stream 41 from the fractionator 40 can be sent to the flare or to waste treatment via stream 43. Alternatively, stream 41 may be sent to a separator 42 where butane is recovered in stream 44 and reused in the process as the azeotropic agent. Minor amounts of organic compounds and water may be present in the reused azeotropic agent. Acetaldehyde is concentrated and recovered in stream 45 and sent to flare or recovered as a byproduct. This removes acetaldehyde from the process and reduces the acetaldehyde in the product. Separator 42 may be a simple vessel or have multiple stages. In some embodiments, separator 42 may be a single or multi-stage extractor and an extractant (such as water) may be used to separate butane. In some embodiments, a series of extractors may be used to produces stream 45 and recovery useful methyl iodide. This allows acetaldehyde to be effectively reduced and/or removed from the process through the formation of an azeotrope.

In another embodiment, there is provided a method for removing aldehydes formed in the production of acetic acid, comprising reacting methanol and carbon monoxide in a suitable liquid phase reaction medium comprising a Group VIII metal catalyst, an organic iodide (e.g. methyl iodide), and water; separating said liquid phase reaction medium, with or without heat, into a volatile phase comprising acetic acid and aldehyde, and a less volatile phase comprising the Group VIII metal catalyst; distilling said volatile phase in a first distillation tower to yield a side draw stream comprising acetic acid and an overhead comprising organic iodide, water, and aldehyde; collecting a condensed portion of the overhead in an overhead decanter receiver to yield an aqueous phase and an organic phase; contacting at least a portion of said organic phase with an azeotropic agent to form a stream containing one or more azeotropes with said aldehyde; and fractionating said stream in a second distillation tower to remove aldehydes.

FIG. 3 shows an embodiment for processing the heavy phase by contacting a portion of the heavy phase with an azeotropic agent comprising butane. In one embodiment, the organic phase may comprise aldehyde in the range of 400 to 3500 ppm. In FIG. 3, the heavy phase of the decanter 17 flows out via stream 24. In some embodiments, stream 24 may comprise a portion of the light phase obtained from the decanter 17. An azeotropic agent comprising butane in stream 47 is combined with stream 24 to form stream 48 which is fed to a fractionator 50, which may be referred to as the second distillation tower. Thus, stream 48 contains one or more azeotropes of aldehyde. In one embodiment, the amount of azeotropic agent combined with stream 24 is sufficient to form azeotropes with more than 60% of the aldehydes, e.g., more than 80% of the aldehydes. The amount of free aldehyde, i.e., aldehyde not present in an azeotrope, is reduced in stream 24. A suitable mixer or agitator may be used to intimately contact the azeotropic agent to promote formation of the azeotropes. In one embodiment, the contacting of stream 47 with stream 24 is controlled at a temperature of greater than or equal to 25° C. to be less than or equal to 120° C., e.g., greater than or equal to 30° C. to less than or equal to 100° C., or greater than or equal to 35° C. to less than or equal to 80° C.

In one embodiment, the second distillation tower fractionates (distills) stream 48 to remove aldehydes in the overhead. The bottom stream from the fractionator 50 contains a significant quantity of methyl iodide and is returned to the reactor in FIG. 1 via stream 49 (return stream). In one embodiment, return stream 49 may be combined with the less volatile phase, which are together returned to the reactor. In one embodiment, the return stream 49 is deficient in aldehydes and azeotropes of aldehyde. Further, the overhead stream 51 from the fractionator 50 can be sent to the flare or to waste treatment via stream 53. The aldehyde azeotrope is carried in the overhead stream 51. In one embodiment, stream 51 may be sent to a separator 54 where azeotropic agent (e.g., butane) is recovered in stream 55 and reused in the process and acetaldehyde is recovered in stream 56 and sent to flare or recovered as a byproduct. In some embodiments, overhead stream 51 may be phased separated prior to being introduced into separator 54.

Hereinafter, the present invention will be better understood in view of the following non-limiting example.

EXAMPLE

A simulation using computer modelling was conducted on the heavy phase processing scheme shown in FIG. 3. A liquid stream containing 17.3% by mass of methyl acetate, 1.9% by mass of acetic acid, 1% by mass of water, 0.2% by mass of methanol, 2550 ppm of acetaldehyde, and the balance was methyl iodide was used as a heavy phase. This liquid stream was mixed with butane at a temperature of 30.2° C. at a pressure of 241 kPa prior to fractionating in a distillation column. The distillation column operated with base temperature of 70.2° C. and a top temperature of 56.9° C. The bottom fraction (residual liquid) contained methyl iodide, less than about 300 ppm of acetaldehyde, and less than 0.0001% by mass of butane. Based on the low butane concentration, the bottom fraction is deficient in the butane-acetaldehyde azeotrope. The bottom fraction owing to the lower concentrations of acetaldehyde can be returned to the carbonylation reactor. As a result of the separation the acetaldehyde was carried overhead with the butane, as part of an azeotrope, and was able to be removed from the process. The overhead was separated in an overhead receiver into an aqueous stream and organic stream.

While the invention has been described with reference to the preferred embodiments, obvious modifications and alterations are possible by those skilled in the related art having the benefits of this disclosure. Therefore, it is intended that the invention include all such modifications and alterations to the full extent that they come within the scope of the following claims or the equivalents thereof.

What is claimed is:

1. A method for removing aldehydes formed in the production of acetic acid, comprising:
    reacting methanol and carbon monoxide in a suitable liquid phase reaction medium comprising a Group VIII metal catalyst, an organic iodide, and water;
    separating said liquid phase reaction medium, with or without heat, into a volatile phase comprising acetic acid and aldehyde, and a less volatile phase comprising said Group VIII metal catalyst;
    distilling said volatile phase in a first distillation tower to yield a side draw stream comprising acetic acid and an overhead comprising organic iodide, water, and aldehyde;
    contacting a portion of said overhead with an azeotropic agent to form one or more azeotropes with at least one of said aldehydes;
    removing said one or more azeotropes to obtain a return stream containing said organic iodide; and
    combining said return stream with said less volatile phase, wherein said return stream is deficient in said one or more azeotropes with aldehyde.

2. The method of claim 1, wherein said azeotropic agent comprises butane.

3. The method of claim 1, wherein said one or more azeotropes are removed by fractionation.

4. The method of claim 1, wherein said overhead stream comprises 1000 to 3000 ppm of acetaldehyde.

5. The method of claim 1, wherein said one or more azeotropes have a boiling point lower than said organic iodide.

6. The method of claim 1, wherein said aldehyde comprises at least one of acetaldehyde, acetone, methyl ethyl ketone, butyraldehyde, crotonaldehyde, 2-ethyl crotonaldehyde, or 2-ethyl butyraldehyde.

7. The method of claim 1, further comprising introducing said combined stream into said liquid phase reaction medium.

8. The method of claim 1, wherein said liquid phase reaction medium comprises an iodide salt.

9. The method of claim 1, wherein said step of removing said one or more azeotropes comprises fractionation, extraction, or phase separation.

10. A method for removing aldehydes formed in the production of acetic acid, comprising:
    reacting methanol and carbon monoxide in a suitable liquid phase reaction medium comprising a Group VIII metal catalyst, an organic iodide, and water;
    separating said liquid phase reaction medium, with or without heat, into a volatile phase comprising acetic acid and aldehyde, and a less volatile phase comprising said Group VIII metal catalyst;
    distilling said volatile phase in a first distillation tower to yield a side draw stream comprising acetic acid and an overhead comprising organic iodide, water, and aldehyde;
    collecting a condensed portion of said overhead in an overhead decanter receiver to yield an aqueous phase and an organic phase;
    contacting at least a portion of said organic phase with an azeotropic agent to form a stream containing one or more azeotropes with at least one of said aldehydes; and
    fractionating said stream in a second distillation tower to remove aldehydes.

11. The method of claim 10, wherein said azeotropic agent comprises butane.

12. The method of claim 11, wherein said aqueous stream comprises 100 to 2500 ppm of acetaldehyde.

13. The method of claim 11, wherein said aldehyde comprises at least one of acetaldehyde, acetone, methyl ethyl ketone, butyraldehyde, crotonaldehyde, 2-ethyl crotonaldehyde, or 2-ethyl butyraldehyde.

14. The method of claim 11, further comprising obtaining a return stream comprising methyl iodide from said fractionating step.

15. A method for removing aldehydes formed in the production of acetic acid, comprising:
    reacting methanol and carbon monoxide in a suitable liquid phase reaction medium comprising a Group VIII metal catalyst, an organic iodide, and water;
    separating said liquid phase reaction medium, with or without heat, into a volatile phase comprising acetic acid and aldehyde, and a less volatile phase comprising said Group VIII metal catalyst;
    distilling said volatile phase in a first distillation tower to yield a side draw stream comprising acetic acid and an overhead comprising organic iodide, water, and aldehyde;
    collecting a condensed portion of said overhead in an overhead decanter receiver to yield an aqueous phase and an organic phase;
    contacting at least a portion of said aqueous phase with an azeotropic agent to form a stream containing one or more azeotropes with at least one of said aldehydes; and
    fractionating at least a portion said stream in a second distillation tower to remove aldehydes.

16. The method of claim 15, wherein said azeotropic agent comprises butane.

17. The method of claim 15, wherein said aqueous stream comprises 100 to 2500 ppm of acetaldehyde.

18. The method of claim 15, wherein said aldehyde comprises at least one of acetaldehyde, acetone, methyl ethyl ketone, butyraldehyde, crotonaldehyde, 2-ethyl crotonaldehyde, or 2-ethyl butyraldehyde.

19. The method of claim 15, further comprising obtaining a return stream comprising said organic iodide from said fractionating step.

* * * * *